United States Patent [19]

Gauhl et al.

[11] 4,334,023
[45] Jun. 8, 1982

[54] PROCESS FOR OBTAINING CHOLESTEROL OXIDASE

[75] Inventors: Helmgard Gauhl, Tutzing; Georg Schawohl, Munich; Hans Seidel; Klaus Beaucamp, both of Tutzing, all of Fed. Rep. of Germany

[73] Assignee: Boehringer Mannheim GmbH, Mannheim-Waldhof, Fed. Rep. of Germany

[21] Appl. No.: 147,460

[22] Filed: May 7, 1980

[30] Foreign Application Priority Data

Jun. 20, 1979 [DE] Fed. Rep. of Germany ....... 2924875

[51] Int. Cl.³ .............................................. C12N 9/04
[52] U.S. Cl. .................... 435/190; 435/886; 435/898; 435/830
[58] Field of Search ........................................ 435/190

[56] References Cited

U.S. PATENT DOCUMENTS 4,093,517  6/1978  Masurekar et al. ................ 435/190

OTHER PUBLICATIONS

Fukuda et al., Chem. Pharm. Bull., vol. 21 (9) 2057–2060 (1973).

*Primary Examiner*—Lionel M. Shapiro
*Attorney, Agent, or Firm*—Felfe & Lynch

[57] ABSTRACT

The present invention provides a process for obtaining cholesterol oxidase, wherein *Streptomyces griseofuscus* DSM 40191, *Streptomyces hygroscopicus* 40771, *Streptomyces acidomyceticus* DSM 40798 and/or *Arthrobacter paraffinens* DSM 312 are cultured and the enzyme obtained from the culture supernatant and/or the cells.

8 Claims, No Drawings

PROCESS FOR OBTAINING CHOLESTEROL OXIDASE

The present invention is concerned with a process for obtaining cholesterol oxidase from micro-organisms.

The enzyme cholesterol oxidase has achieved great importance since it enables a very specific and sensitive quantitative determination of cholesterol to be carried out, especially in body fluids. The enzyme is normally obtained from micro-organisms which are cultured on a medium which contains one or more cholesterol oxidase inducers.

However, in spite of the addition of inducers, the maximum achievable cholesterol oxidase activities are, in comparison with other enzymes, relatively low so that there is a need for the discovery of processes which permit a further increase of the obtainable liter activities of this enzyme.

As inducers there are used those substances which themselves represent a substrate for the desired enzyme or are chemically closely related with such a substrate. The addition of a cholesterol oxidase inducer is necessary in order to achieve higher activity yields since, without the presence of an inducer, it is completely uneconomic for micro-organisms to form an enzyme for which there is no use, the use being the enzymatic decomposition of the substance functioning as inducer. Without an inducer, various micro-organisms admittedly also form cholesterol oxidase but not in an amount which makes working up worthwhile but, as a rule, only in an amount of up to about 100 U/liter.

As a rule, the use of a cholesterol oxidase inducer admittedly increases the activity yield of desired enzyme but is also complicates the process and has a negative influence on the reproducability. The reason for this is that inducers used have a strongly lipophilic character and, therefore, can only be incorporated with difficulty in reproducably fine and uniform distribution in the aqueous culture medium for the micro-organisms. It would, therefore, be desirable to find a process which permits cholesterol oxidase to be obtained without the addition of inducer in culture in yields which correspond at least to those which, at the present time, can be achieved with processes with the addition of an inducer.

It is an object of the present invention wholly or partly to overcome the above problems. In particular, it is an object of the present invention to provide a process for obtaining cholesterol oxidase which permits higher enzyme yields to be achieved than in the case of the known processes. Another object of the present invention is to provide such a process which makes it possible to avoid the use of a cholesterol oxidase inducer.

Thus, according to the present invention, there is provided a process for obtaining a cholesterol oxidase, wherein *Streptomyces griseofuscus* DSM 40191, *Streptomyces hygroscopicus* DSM 40771, *Streptomyces acidomyceticus* DSM 40798 and/or *Arthrobacter paraffinens* DSM 312 is cultured and the enzyme obtained from the culture supernatant and/or from the cells.

With the micro-organisms employed according to the present invention, activities are achieved which lie far above the values previously achievable. Whereas hitherto maximum activities of 2000 U/liter were achieved, according to the present invention, activities are achieved of up to about 6000 U/liter of culture solution. However, it is especially surprising that these superior yields can be achieved without the addition of a cholesterol oxidase inducer. Therefore, the micro-organisms used according to the present invention represent constitutive cholesterol oxidase formers which, in comparison with the best known constitutive cholesterol oxidase formers, give an enzyme activity which is up to 60 times greater. These statements of activity refer to fermentation media with a biomass content of about 5 to 10 g./liter.

The micro-organisms employed in the process according to the present invention also give up the enzyme to the culture supernatant, the total activity in the culture supernatant being, as a rule, greater than the activity in the crude extract which is obtained by digestion of the cells.

The micro-organisms used in the process according to the present invention are cultured on the nutrient media normally employed for Streptomycetes under aerobic conditions and preferably in a shake culture. A culture medium which is especially preferred contains 10 to 30 g./liter of soluble starch, 2 to 10 g./liter of peptone (meat) and 2 to 10 g./liter of yeast extract, as well as the usual salts, trace elements and vitamins. When using such a medium, as a rule, maximum yields are obtained in a period of culturing of from 2 to 5 days.

Due to the achievement of high cholesterol oxidase activities, the present invention makes it possible considerably to cheapen the production process. Of especial advantage is thereby the possibility that a cholesterol oxidase inducer can be omitted, which results not only in a further cheapening of the process but also considerably improves the reproducability thereof.

The following Examples are given for the purpose of illustrating the present invention:

EXAMPLE 1

*Streptomyces griseofuscus* DSM 40191 (ATCC 23916; IFO 12870) is cultured in a medium with the following composition:

20 g./liter soluble starch,
5 g./liter peptone (meat),
4 g./liter yeast extract (Difco),
2 g./liter calcium carbonate,
1 g./liter potassium nitrate,
0.5 g./liter dipotassium hydrogen phosphate,
1.03 g./liter magnesium sulphate heptahydrate,
0.5 g./liter sodium chloride,
0.02 g./liter ferrous sulphate heptahydrate.

The micro-organism is cultured for 2 days in 10 ml. of the medium in a 100 ml. Erlenmeyer flask and then transferred into 40 ml. of the same medium in a 250 ml. Erlenmeyer flask. Subsequently, it is cultured at 30° C., while shaking. After 3 days, a sample is removed and the activity of the cholesterol oxidase is tested in the culture supernatant and in the crude extract. The crude extract is obtained by centrifuging 5 ml. of culture solution, washing the biomass with 0.5 M phosphate buffer (pH 7), resuspending in 5 ml. of the same buffer and digesting by the addition of 0.2 ml. 10% "Triton" X100 solution. After standing for 10 minutes at ambient temperature, the digest is centrifuged and the supernatant is obtained as a crude extract.

In order to carry out the activity determination, the formation of cholestenone is measured on the basis of the increase of the extinction at 240 nm and at pH 7.5 in 0.5 mol/liter phosphate buffer. For control purposes, in each case a blank is measured without the addition of cholesterol. The following results are determined:

total U/liter of culture solution: 5741
proportion in the crude extract U/liter: 1118
proportion in the culture supernatant U/liter: 4623.

EXAMPLE 2

The process of Example 1 is repeated but with the use of *Streptomyces hygroscopicus* DSM 40771 (ATCC 10976). The determinations are carried out after culturing for 3 and 4 days. The following activities are obtained:

| total culturing period in days | total U/l. | crude extract U/l. | culture supernatant U/l. |
| --- | --- | --- | --- |
| 3 | 4765 | 1260 | 3505 |
| 4 | 5223 | 1423 | 3800 |

When culturing is carried out in the presence of 2% cholesterol as inducer, the activity yield is reduced to scarcely one half.

EXAMPLE 3

The process of Example 1 is repeated but with the use of *Streptomyces acidomyceticus* DSM 40798 (ATCC 11611; IFO 3125). The following Table shows the results obtained after culturing periods of 3 and 4 days:

| total culturing period in days | total U/l. | crude extract U/l. | culture supernatant U/l. |
| --- | --- | --- | --- |
| 3 | 1656 | 721 | 935 |
| 4 | 2052 | 711 | 1341 |

When carrying out the culturing in the presence of 2% cholesterol as inducer, the activity yield is increased by 50%.

EXAMPLE 4

The process of Example 1 is repeated but with the use of *Arthrobacter paraffinens* DSM 312 (ATCC 15591) and with the addition to the medium of 3% cholesterol in the form of a suspension in a yeast extract (total 10 g./liter). After a culturing period of 4 days, 4470 U/liter are found in the crude extract. A considerable activity is also ascertained in the culture supernatant.

It will be understood that the specification and examples are illustrative, but not limitative of the present invention and that other embodiments within the spirit and scope of the invention will suggest themselves to those skilled in the art.

What is claimed is:

1. Process for the preparation of cholesterol oxidase, which comprises culturing at least one micro-organism from the group consisting of
   *Streptomyces griseofuscus* DSM 40191,
   *Streptomyces hygroscopicus* 40771,
   *Streptomyces acidomyceticus* DSM 40798; and
   *Arthrobacter paraffinens* DSM 312,
and recovering cholesterol oxidase from the culture.

2. Process as claimed in claim 1 wherein said cholesterol oxidase is obtained from the culture supernatant.

3. Process as claimed in claim 1 wherein said cholesterol oxidase is obtained from the culture cells.

4. Process as claimed in claim 1 wherein said culturing is carried out in a medium not containing a cholesterol oxidase inducer.

5. Process as claimed in claim 1 wherein the microorganism is *Streptomyces griseofuscus* DSM 40191.

6. Process as claimed in claim 1 wherein the microorganism is *Streptomyces hygroscopicus* 40771.

7. Process as claimed in claim 1 wherein the microorganism is *Streptomyces acidomyceticus* DSM 40798.

8. Process as claimed in claim 1 wherein the microorganism is *Arthrobacter paraffinens* DSM 312.

* * * * *